(12) United States Patent
Na et al.

(10) Patent No.: US 9,954,134 B2
(45) Date of Patent: Apr. 24, 2018

(54) OPTICAL BIOSENSOR AND MANUFACTURING METHOD THEREOF

(71) Applicant: Samsung Electronics Co., Ltd., Suwon-Si, Gyeonggi-Do (KR)

(72) Inventors: Kyoung Won Na, Seoul (KR); Yoon Dong Park, Osan-si (KR); Sung Dong Suh, Seoul (KR); Dong Mo Im, Jindo-gun (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 408 days.

(21) Appl. No.: 14/072,118

(22) Filed: Nov. 5, 2013

(65) Prior Publication Data

US 2014/0134712 A1 May 15, 2014

(30) Foreign Application Priority Data

Nov. 9, 2012 (KR) ........................ 10-2012-0126486

(51) Int. Cl.
*H01L 31/18* (2006.01)
*G01N 21/77* (2006.01)
*G01N 33/483* (2006.01)

(52) U.S. Cl.
CPC ......... *H01L 31/18* (2013.01); *G01N 21/7746* (2013.01); *G01N 33/483* (2013.01)

(58) Field of Classification Search
None
See application file for complete search history.

(56) References Cited

U.S. PATENT DOCUMENTS

| 5,494,833 | A | 2/1996 | Martin et al. |
| 6,583,399 | B1 | 6/2003 | Hunziker et al. |
| 2004/0146431 | A1 | 7/2004 | Scherer et al. |
| 2011/0243492 | A1* | 10/2011 | Na ........................ G02F 1/025 385/3 |

OTHER PUBLICATIONS

Farahi et al., Multiplexed fibre optic sensors using ring interferometers, Journal of Modern Optics, 1989, 36(3) 337-348.*
Muzammil Iqbal, "Label-Free Biosensor Arrays Based on Silicon Ring Resonators and High-Speed Optical Scanning Instrumentation", IEEE Journal of Selected Topics in Quantum Electronics, vol. 16, No. 3, May/Jun. 2010, pp. 654-661.

* cited by examiner

*Primary Examiner* — Melanie Y Brown
*Assistant Examiner* — Richard Moerschell
(74) *Attorney, Agent, or Firm* — Harness, Dickey & Pierce, P.L.C.

(57) ABSTRACT

An optical biosensor, and a method of manufacturing the same, includes a first layer, a second layer stacked on the first layer, a first grating coupler within the first layer and the second layer, and a second grating coupler within the first layer. The first grating coupler is configured to couple a light pattern provided to a front side of the optical biosensor. The second grating coupler is configured to output the light pattern coupled by the first grating coupler to a photoelectric conversion element on a rear side of the optical biosensor.

7 Claims, 14 Drawing Sheets

OPTICAL BIOSENSOR AND MANUFACTURING METHOD THEREOF

CROSS-REFERENCE TO RELATED APPLICATIONS

This application claims the benefit of priority under 35 U.S.C. § 119 from Korean Patent Application No. 10-2012-0126486, filed on Nov. 9, 2012, in the Korean Intellectual Property Office, the entire contents of which are herein incorporated by reference.

BACKGROUND

Field

Example embodiments of inventive concepts relate to an optical biosensor, and more particularly, to an optical biosensor including a first grating coupler of an input terminal, the first grating coupler being configured to couple a light pattern provided to a front side of the optical biosensor, and a second grating coupler of an output terminal configured to output a light pattern, the second grating coupler being coupled to the first grating coupler and being configured to couple a light pattern to a photoelectric conversion device formed at the rear of the optical biosensor.

Description of Related Art

A biosensor is a sensor for measuring the amount of desired material by immobilizing biological material that can react to specific substances with specific and selective combination (e.g., enzyme, antigen-antibody, ligand, or deoxyribonucleic acid (DNA)) to a specific medium by means of light, electric chemical, fluorescence, surface plasmon resonance (SPR), field-effect transistor (FET), quartz crystal microbalance (QCM), or heating.

The optical biosensor is a kind of the biosensor, and can detect the state or the amount of biomaterial through light.

SUMMARY

Example embodiments relate to an optical biosensor, and more particularly, to an optical biosensor including a first grating coupler of an input terminal, the first grating coupler being configured to couple a light pattern provided to a front side of the optical biosensor, and a second grating coupler of an output terminal configured to output a light pattern, the second grating coupler being coupled to the first grating coupler and being configured to couple a light pattern to a photoelectric conversion device formed at the rear of the optical biosensor.

According to example embodiments of the inventive concepts, an optical biosensor includes a first layer, a second layer stacked on the first layer, a first grating coupler within the first layer and the second layer, wherein the first grating coupler is configured to couple a light pattern provided to a front side of the optical biosensor, and a second grating coupler within the first layer, wherein the second grating coupler is configured to output the light pattern coupled by the first grating coupler to a photoelectric conversion element on a rear side of the optical biosensor.

The depth of the first grating coupler and the depth of the second grating coupler may be same, and the thickness of the first layer may be identical to the depth of the second grating coupler. The optical biosensor may further include a light resonator configured to sense biomaterial by using the light pattern coupled by the first grating coupler. The light resonator may be a ring resonator.

The light pattern may be output from the light resonator, and the optical biosensor may further include an optical spectrometer configured to disperse the light pattern. The optical spectrometer may include a plurality of ring resonators. The first grating coupler and the second grating coupler may be formed on opposing sides of the optical biosensor.

According to example embodiments of the inventive concepts, a bio-image sensor includes the optical biosensor, the photoelectric conversion device coupled to the optical biosensor, a metal line layer below the photoelectric conversion device, and a sustain wafer layer below the metal line layer, wherein the optical biosensor is between the metal line layer and the sustain wafer layer.

According to example embodiments of the inventive concepts, a method for manufacturing an optical biosensor includes stacking a first layer on a first side of an insulating layer, wherein a photoelectric conversion device is on a second side of the insulating layer, patterning the stacked first layer in a first pattern of a first grating coupler to be formed on the insulating layer, filling the first pattern with an isolation material, polishing the isolation material on the first layer to form the first grating coupler, stacking a second layer on the first layer, and patterning the stacked first and second layers in a second pattern of a second grating coupler to be formed in the stacked first and second layers to form the second grating coupler. The first grating coupler is configured to output a coupled light pattern to the photoelectric conversion device, and the photoelectric conversion device is on a rear side of the optical biosensor. The second grating coupler is configured to couple a light pattern provided to a front side of the optical bio sensor.

The depth of the first grating coupler and the depth of the second grating coupler may be same, and the thickness of the first layer may be identical to the depth of the first grating coupler. The first layer and the second layer may each be composed of at least one selected from the group consisting of Si, $Si_3N_4$, and a polymer. The insulating layer may be composed of $SiO_2$.

The polishing of the isolation material may include chemical mechanical polishing (CMP). The first layer may be thicker than the second layer. The optical biosensor according to example embodiments may be manufactured by the method.

According to yet other example embodiments of the inventive concepts, an optical biosensor includes a grating coupling system. The grating coupling system includes a bio-sensing region, a first grating pattern extending from the bio-sensing region to an input terminal on a first surface of the grating coupling system, and a second grating pattern extending from the bio-sensing region to a surface of the grating coupling system other than the first surface. The first grating pattern is configured to couple a light pattern output from the input terminal to the bio-sensing region. The second grating pattern is configured to couple the light pattern output from the bio-sensing region to a photoelectric conversion device.

The bio-sensing region may include at least two layers. The first grating pattern may extend through a first layer of the at least two layers and partially extend within a second layer of the at least two layers. The second grating pattern may extend from a bottom surface of the first layer through the second layer.

A depth of the second grating pattern may be equal to a thickness of the second layer.

The first grating pattern and the second grating pattern respectively may extend in a direction parallel to each other, and a depth of the first grating pattern may partially overlap with a depth of the second grating pattern along the direction.

The bio-sensing region may be interposed between the first grating pattern and the second grating pattern, and the first grating pattern and the second grating pattern may extend to opposing surfaces of the grating coupling system.

A width of the first grating pattern, a width of the second grating pattern and a width of the bio-sensing region may collectively equal a width of the grating coupling system.

BRIEF DESCRIPTION OF THE DRAWINGS

Exemplary embodiments of the inventive concept will be more clearly understood from the following detailed description taken in conjunction with the accompanying drawings in which.

DETAILED DESCRIPTION OF EXAMPLE EMBODIMENTS

Figure 1:
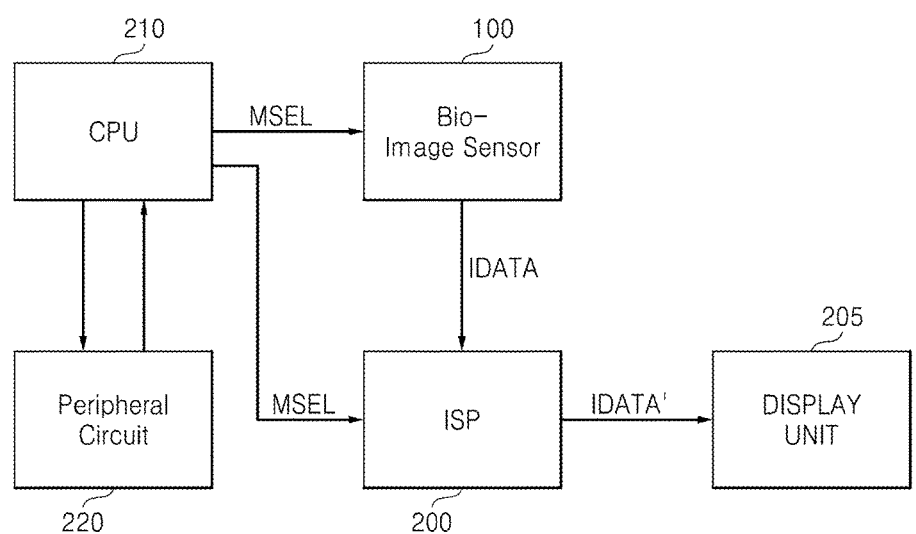
FIG. 1 is a block diagram of a bio-sensing system according to example embodiments of the inventive concepts.

Various example embodiments will be described more fully hereinafter with reference to the accompanying drawings, in which some example embodiments are shown. Inventive concepts may, however, be embodied in many different forms and should not be construed as limited to the example embodiments set forth herein. Rather, example embodiments are provided so that this disclosure will be thorough and complete, and will fully convey the scope of inventive concepts to those skilled in the art. In the drawings, the sizes and relative sizes of layers and regions may be exaggerated for clarity. Like numerals refer to like elements throughout.

It will be understood that, although the terms first, second, third etc. may be used herein to describe various elements, these terms should not be limited by these terms. These terms are used to distinguish one element from another. Thus, a first element discussed below could be termed a second element without departing from the teachings of the inventive concepts. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacently" versus "directly adjacently," etc.).

The terminology used herein is for the purpose of describing particular example embodiments only and is not intended to be limiting of the inventive concepts. As used herein, the singular forms "a," "an" and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which inventive concepts belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Example embodiments relate to an optical biosensor, and more particularly, to an optical biosensor including a first grating coupler of an input terminal, the first grating coupler being configured to couple a light pattern provided to a front side of the optical biosensor, and a second grating coupler of an output terminal configured to output a light pattern, the second grating coupler being coupled to the first grating coupler and being configured to couple a light pattern to a photoelectric conversion device formed at the rear of the optical biosensor.

FIG. 1 is a block diagram of a bio-sensing system according to example embodiments of the inventive concepts.

Referring to FIG. 1, a bio-sensing system 10 includes a bio-image sensor 100, an image signal processor (ISP) 200, a display unit 205, a central processing unit (CPU) 210, and a peripheral circuit 220.

The bio-sensing system 10 may be embodied into a system on chip (SoC) according to example embodiments. The bio-image sensor 100, the ISP 200, and the CPU 210 may be embodied into a system on chip (SoC) according to other example embodiments. The bio-image sensor 100 may be embodied into a separate chip according to yet further example embodiments.

The bio-sensing system 10 may include a function of biosensor detecting status, concentration of biological material (e.g., enzymes, antigens, antibodies, ligands, deoxyribonucleic acid (DNA), or viruses), or changes of the status and concentration, a function of color sensor that can obtain color information of an object, a function of depth sensor that can obtain depth information of the object, and/or a function of motion sensor that can obtain motion information by sensing movement of the object. At this time, the bio-image sensor 100 may select one function among the biosensor function, the color sensor function, the depth sensor function, or the motion sensor function according to a mode select signal MSEL transmitted from the CPU 210 and transmit image data IDATA generated according to the selection result to the ISP 200.

When the bio-image sensor 100 performs the function of depth sensor, the bio-image sensor may include a time of flight (TOF) sensor. When the bio-image sensor performs the function of motion sensor, the bio-image sensor may include a dynamic vision sensor (DVS).

The ISP 200 receives image data IDATA, processes the received image data IDATA, and generates the processed image data IDATA'. The ISP 200 may process or compose the image data IDATA in a unit of frame. The ISP 200 may process image data IDATA including bio-information (or bio-image), image data IDATA including color information (or color image), image data IDATA corresponding to depth information (or depth image), or image data IDATA corresponding to motion information of an object (or motion image) in different ways with each other. Also, the ISP 200 may correct light and shade, contrast, chroma, or the like of image data IDATA. The ISP 200 may transmit the processed image data IDATA' to a display unit 205.

The display unit 205 denotes all kinds of devices that can display the processed data IDATA'.

The CPU 210 interprets data transmitted from the peripheral circuit 220, generates a mode select signal MSEL based on the result of the interpretation, and transmits the generated mode select signal MSEL to the image sensor 100 and the ISP 200.

The peripheral circuit 220 provides data generated according to the state or various inputs of the bio-sensing system 10 to the CPU 210. The peripheral circuit 220 may be embodied into an input interface. At this time, the peripheral circuit 220 provides data generated according to a user's input to the CPU 210. The input interface may be an input device such as button, touch screen, or mouse. The CPU 210 generates a mode select signal MSEL based on the data.

According to other example embodiments, the peripheral circuit 220 may be embodied into an application execution module. At this time, the peripheral circuit 220 embodied as an application execution module monitors execution of a specific application and transmits data generated according to the result of monitoring to the CPU 210. The CPU 210 may generate a mode select signal MSEL based on the data. For example, the specific application may be an application for checking the condition of human body, but the embodiment is not restricted thereto.

Figure 2:
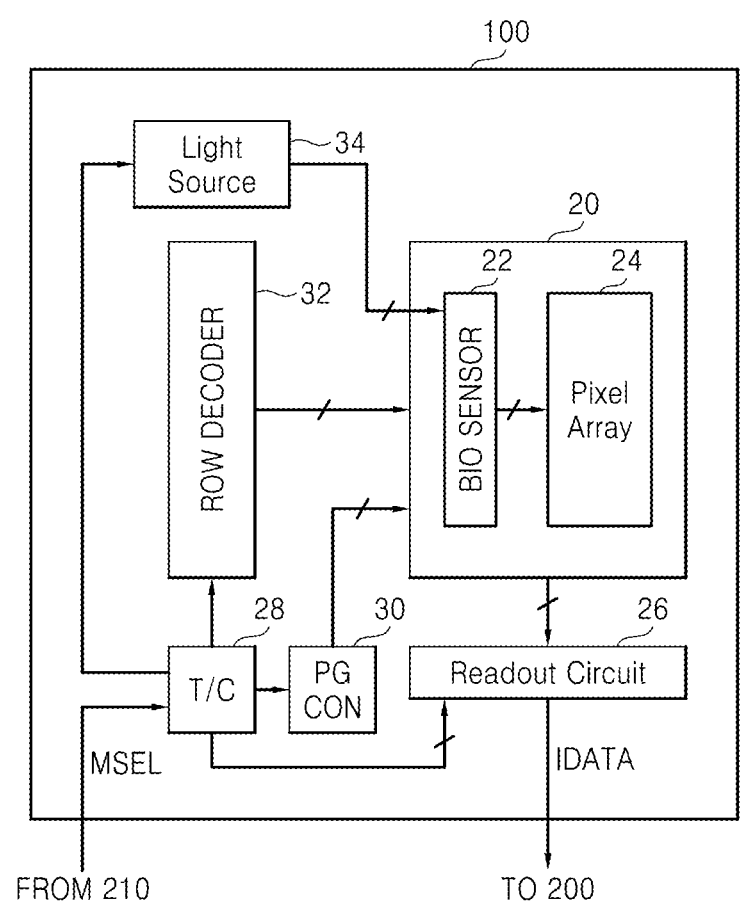
FIG. 2 is a block diagram of a bio-image sensor shown in FIG. 1.

FIG. 2 is a block diagram of the bio-image sensor shown in FIG. 1 according to example embodiments of the inventive concepts.

Referring to FIGS. 1 and 2, the bio-image sensor 100 includes a sensor array 20, a readout circuit 26, a timing controller 28, a photo gate controller 30, a row decoder 32, and a light source driver 34. The bio-image sensor 100 may further include an IR pass filter in some embodiments.

FIG. 2 explains a case that the biosensor array 20 is combined to a time of flight (TOF) sensor as an example, but the embodiment is not restricted thereto.

The bio-image sensor 100 obtains image data IDATA corresponding to depth information (or a depth image) of an object or bio-information (or a bio-image) related to biomaterial by using a time of flight (TOF) principle according to a mode select signal MSEL. In some example embodiments, the bio-image sensor 100 may operate to obtain image data IDATA corresponding to bio-information related biomaterial regardless of the mode select signal MSEL.

The sensor array 20 may include a biosensor array 22 and an image sensor pixel array 24. The biosensor array 22 may include a plurality of biosensors, and the image sensor pixel array 24 may include a plurality of image sensor pixels (for example, TOF sensor pixels).

FIG. 2 illustrates the biosensor array 22 and the image sensor pixel array 24 separately for convenience of explanation, but the biosensor array 22 and the image sensor pixel array 24 may have stacked structure, and the structure will be described in FIGS. 3 through 11 in detail.

Each biosensor in the biosensor array 22 receives a light pattern provided by a light source 34 and outputs the light pattern having a wavelength characteristics changed by biomaterial to image sensor pixels of the image sensor pixel array.

The image sensor pixels of the image sensor pixel array 24 generates pixel signals based on the light pattern output from the biosensor array 22 and transmits the generated pixel signals to the readout circuit 26.

The readout circuit 26 generates image data IDATA based on the pixel signals output from the pixel array 24. The timing controller 28 controls the components of the image sensor 100 (the readout circuit 26, the photo gate controller 30, the row decoder 32, and/or the light source 34) based on a mode select signal MSEL transmitted from the CPU 210.

The photo gate controller 30 generates photo gate control signals and transmits the generated photo gate control signals to the image sensor pixel array 24 under the control of the timing controller 28. In some example embodiments, the bio-image sensor 100 may not include the photo gate controller 30.

The row decoder 32 performs decoding to a plurality of row control signals output from the timing controller 28, for example, row address signals, and drives a specific row line included in the image sensor pixel array 24 according to the result of decoding. The row decoder 32 may denote the concept including a row driver for driving the row line.

The light source 34 generates a light pattern according to the control of the timing controller 28. The light source 34 may denote the concept including a light source driver for controlling the generating a light pattern.

In case that the bio-image sensor 100 operates as a depth sensor, the light source 34 radiates the modulated light pattern, for example, infrared ray, to an object outside the bio-image sensor 100. In case that the bio-image sensor 100 operates as a biosensor, the light source 34 outputs a light pattern to the biosensor array 22 through a light path, for example, optical fiber or the like.

Figure 3:
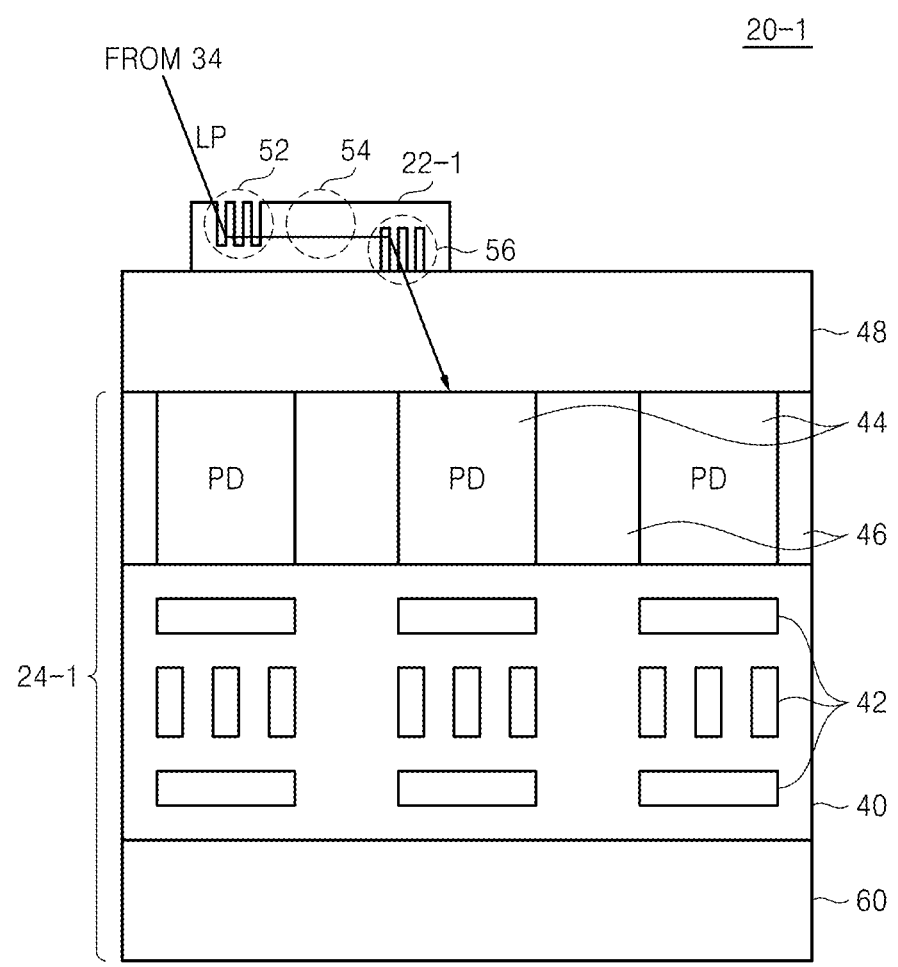
FIG. 3 is a cross-sectional view of a part of the sensor array shown in FIG. 2 according to example embodiments of the inventive concepts.

FIG. 3 is a cross-sectional diagram of a part of the sensor array shown in FIG. 2 according to example embodiments of the inventive concepts.

For convenience of explanation, the sensor array includes a biosensor and three image sensor pixels, but example embodiments are not limited thereto.

Referring to FIGS. 2 and 3, the sensor array 20-1 includes the biosensor 22-1, an insulating layer 48, and an image sensor pixel layer 24-1.

The biosensor 22-1 includes a first grating coupler 52, a bio-sensing region 54, and a second grating coupler 56. The first grating coupler 52 performs coupling on the light pattern LP transmitted to the front (or, light-receiving portion) of the biosensor 22-1 from the light source 34.

The bio-sensing region 54 changes a wavelength characteristics of the coupled light pattern LP coupled by the first grating coupler 52 according to biomaterial.

The second grating coupler 56 outputs the light pattern LP passed through the bio-sensing region 54 to a photoelectric conversion device 44. The second grating coupler 56 outputs the light pattern LP passed through the bio-sensing region 54 to more than two photoelectric conversion devices 44.

The insulating layer 48 insulates the biosensor 22-1 from the image sensor pixel layer 24-1 electrically. The insulating layer 48 may be composed of $SiO_2$.

The image sensor pixel layer 24-1 may include a metal line layer 40, photoelectric conversion devices 44 (for example, photo diodes (PD)), and wells. The image sensor pixel layer 24-1 may further include a sustain wafer layer 60.

The metal line layer 40 includes electric wires, that is, metal lines 42, necessary for the operation of the bio-image sensor 100.

The photoelectric conversion devices 44 receives light patterns transmitted from the biosensor 22-1 and converts the received light patterns into an electric signal. Each of the photoelectric conversion devices 44 may be embodied into a photo transistor, a photo gate, or pinned photo diode (PPD).

Each of the wells 46 is formed between the photoelectric conversion devices 44 and makes isolation between the photoelectric conversion devices 44 electrically. The sustain wafer layer 60 forms a supporting layer on the bottom of the metal line layer 40. The sustain wafer layer 60 may denote a dummy substrate.

FIGS. 4 through 9 are diagrams for a method for manufacturing the biosensor shown in FIG. 3.

Figure 4:
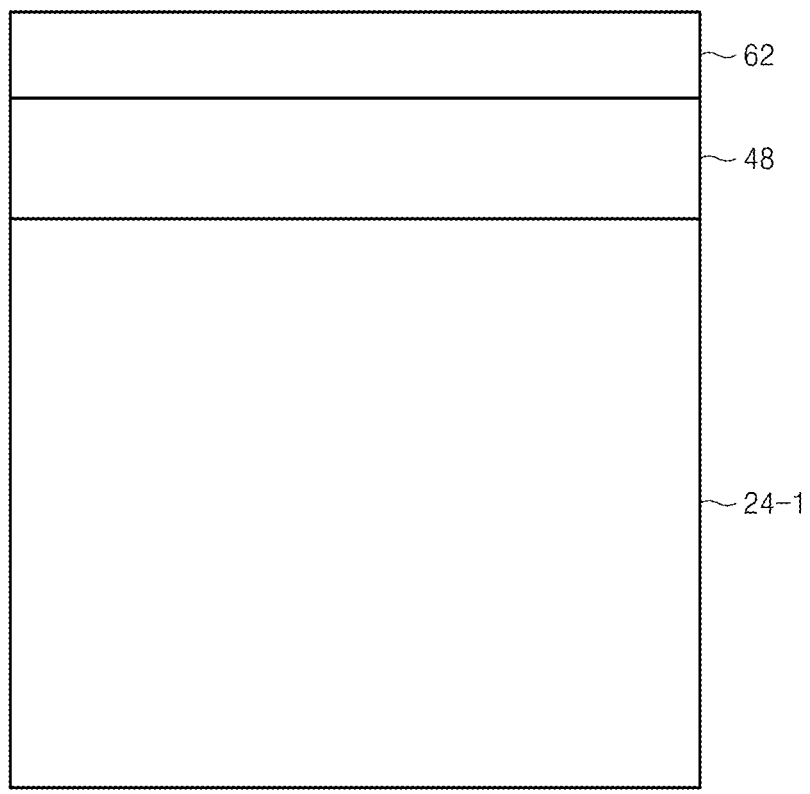
FIGS. 4 through 9 are diagrams for explaining a method for manufacturing a biosensor shown in FIG. 3.
Figure 5:
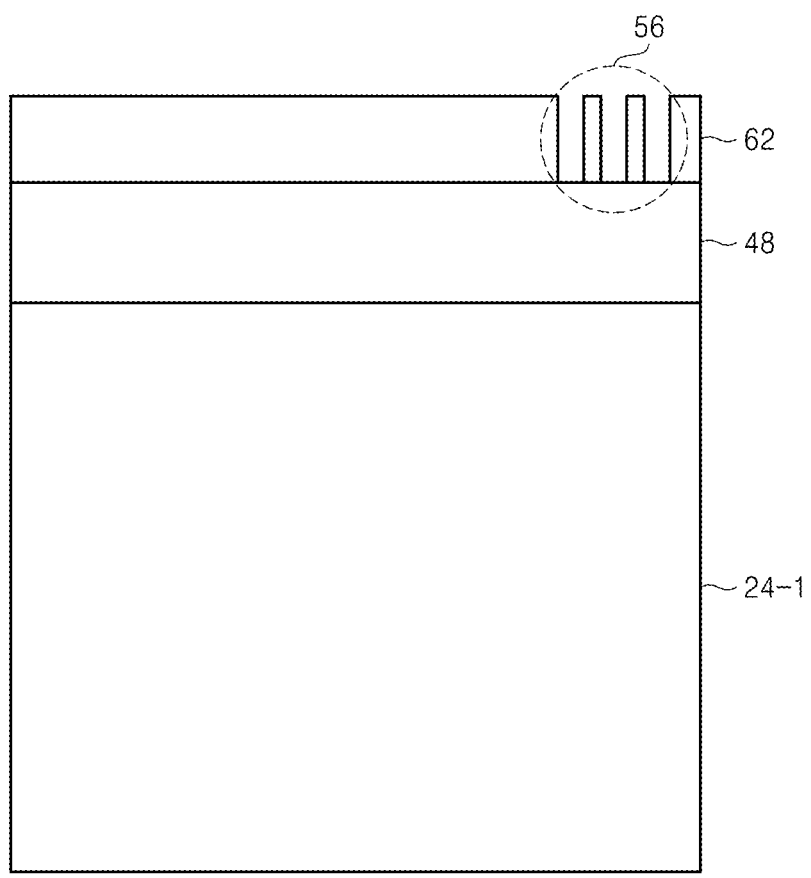

Referring to FIGS. 4 and 5, a first layer 62 is stacked on the insulating layer 48 and undergoes patterning of a pattern of the second grating coupler 56 at one side (for example, right side) of the stacked first layer 62.

Figure 6:
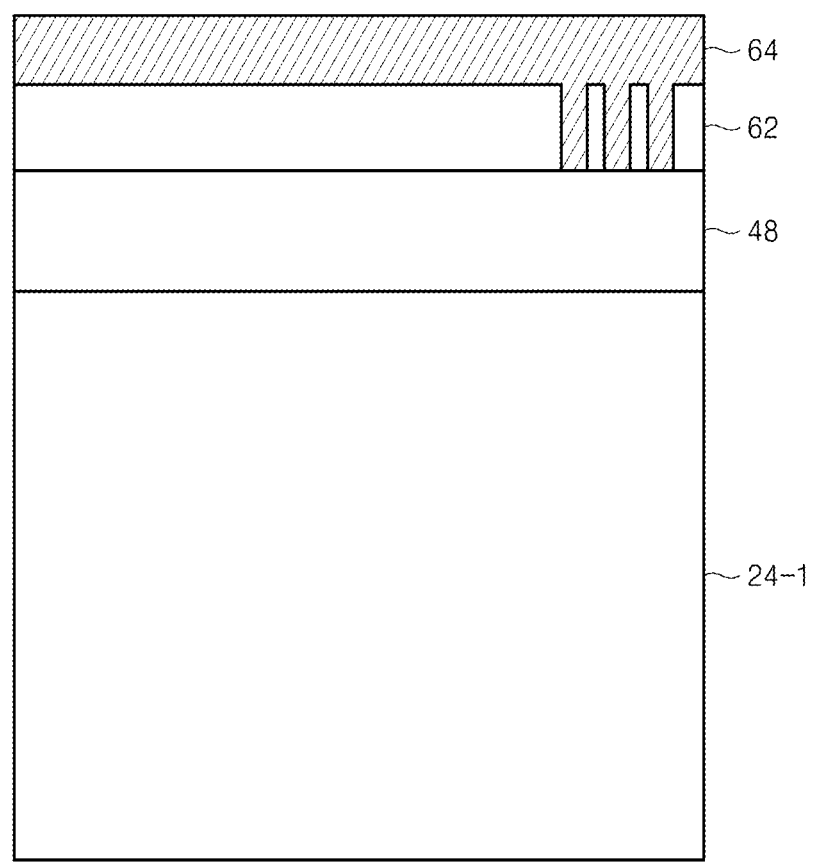
Figure 7:
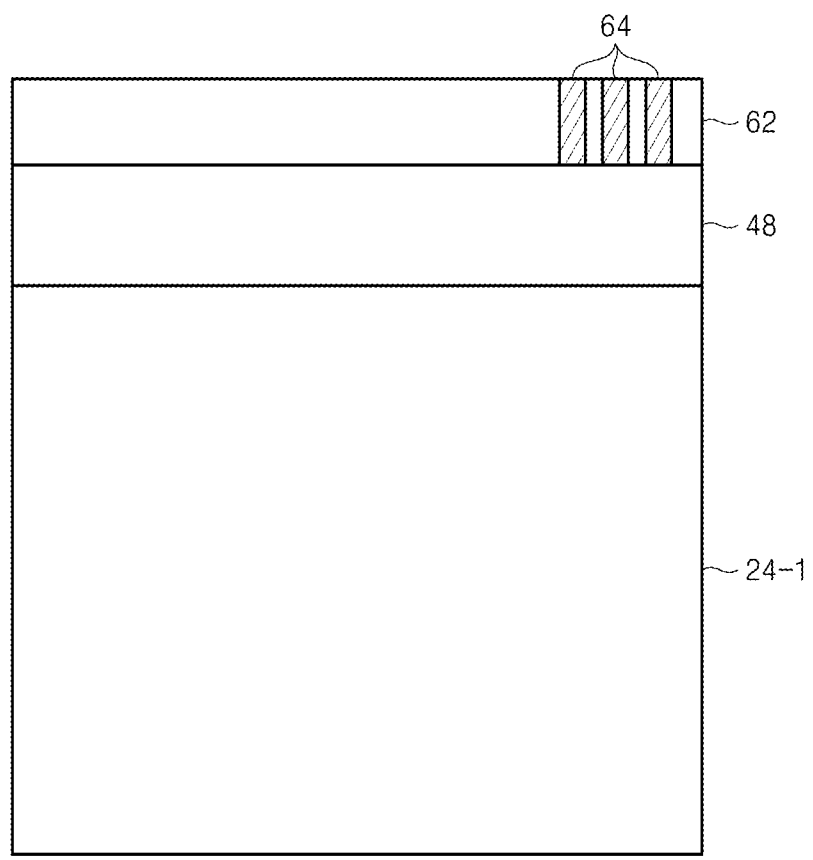

Referring to FIGS. 6 and 7, the pattern of a second grating coupler 56 is filled with isolation material 64. The isolation material 64 stacked on the first layer 62 and may be polished. The polishing may be chemical mechanical polishing (CMP). After the polishing, the pattern of the second grating coupler 56 is filled with the isolation material 64.

Figure 8:
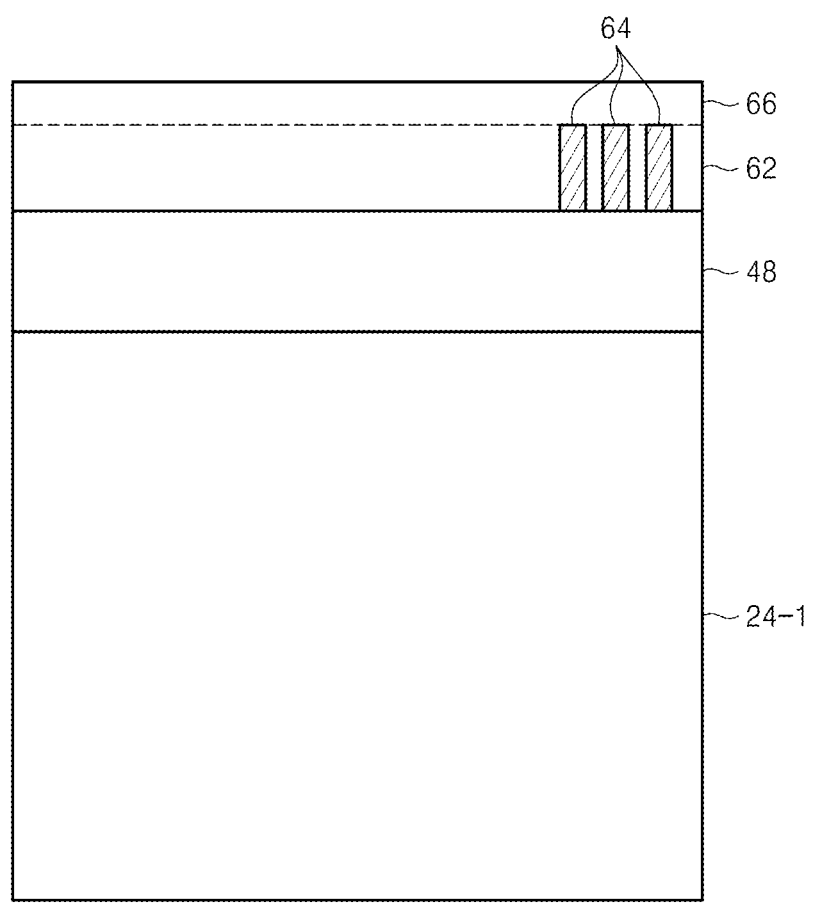
Figure 9:
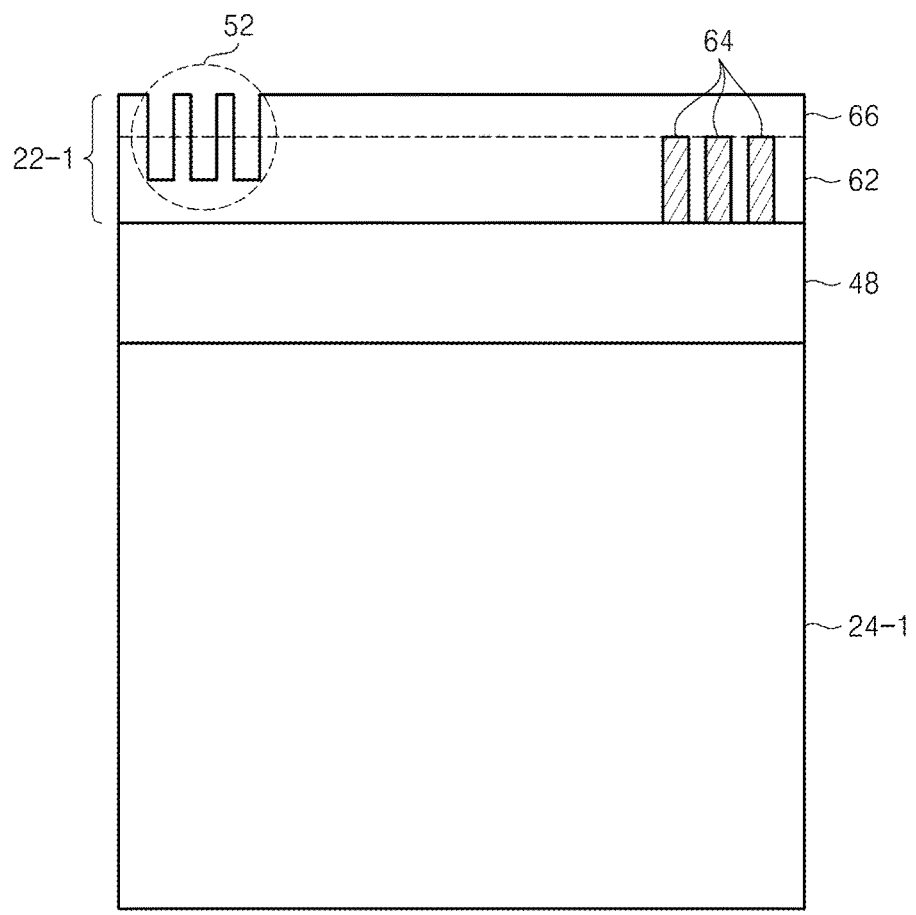

Referring to FIGS. 8 and 9, a second layer 66 is stacked on the first layer 62, and the second layer 66 undergoes patterning of a pattern of a second grating coupler 56. The first grating coupler 52 may be formed on the other side of the second grating coupler 56.

The first layer 62 and the second layer 66 may be composed of Si, $Si_3N_4$, or polymer, and the thickness of the first layer 62 may be thicker than the thickness of the second layer 66. The pattern depth of the first grating coupler 52 and the pattern depth of the second grating coupler 56 may be same, and the pattern depth of the second grating coupler 56 may be same to the thickness of the first layer 62.

Figure 10:
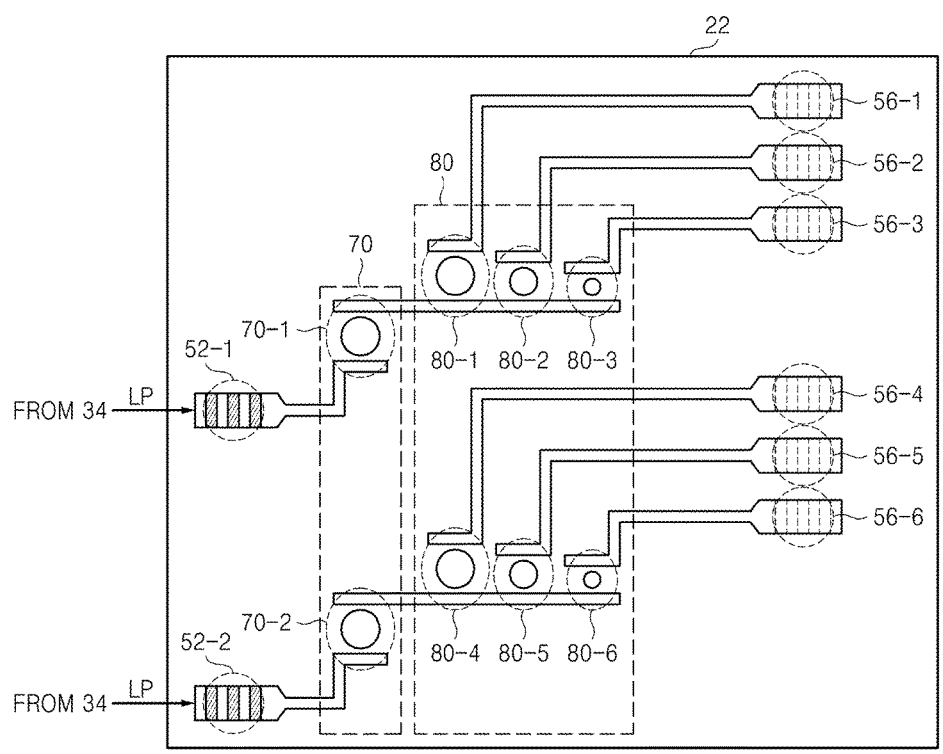
FIG. 10 is a plan view of the biosensor array shown in FIG. 2 according to example embodiments of the inventive concepts.

FIG. 10 is a plan view of the biosensor array shown in FIG. 2 according to example embodiments of the inventive concepts.

Referring to FIGS. 2 and 10, processing paths of the light patterns LP may be etched as shown in FIG. 10 after the biosensor array 20 was formed according to the process of FIGS. 4 through 9.

The biosensor array 22 includes a sensing path 70 and an optical spectrometer (or, spectroscope) 80. The sensing path 70 may include a plurality of sub sensing paths 70-1 and 70-2.

The light pattern LP undergone coupling through the first grating coupler 52-1 may have a different wavelength characteristic (for example, a different wavelength band) while passing through the sub sensing path 70-1, for example, a ring resonator, and only a part of frequency band of the light pattern LP having the changed wavelength characteristic passes through the sub sensing path 70-1. The sub sensing path 70-1 may be embodied into a light resonator besides the ring resonator.

The light pattern LP passed though the sub sensing path 70-1 outputs elements of the light pattern LP having a different wavelength band to each of the second grating coupler 56-1, 56-2, or 56-3 by using a plurality of wavelength selection resonator 80-1 through 80-3 (for example, ring resonators) included in the optical spectrometer 80.

The elements of the light patterns LP a having different wavelength band provided to each of the second grating coupler 56-1, 56-2, or 56-3 are output into the image sensor pixel array 24.

The first grating coupler 52-2 is identical to the first grating coupler 52-1, and the sub sensing path 70-2 is identical to the sub sensing path 70-1, substantially. A plurality of wavelength selection resonator 80-4 through 80-6 are identical to the plurality of wavelength selection resonator 80-1 through 80-3, and the second grating couplers 56-4 through 56-6 are identical to the second grating couplers 56-1 through 56-3, substantially.

The light path of the light pattern LP of FIG. 10 is an example, and the number of the light path may be changed.

Figure 11:
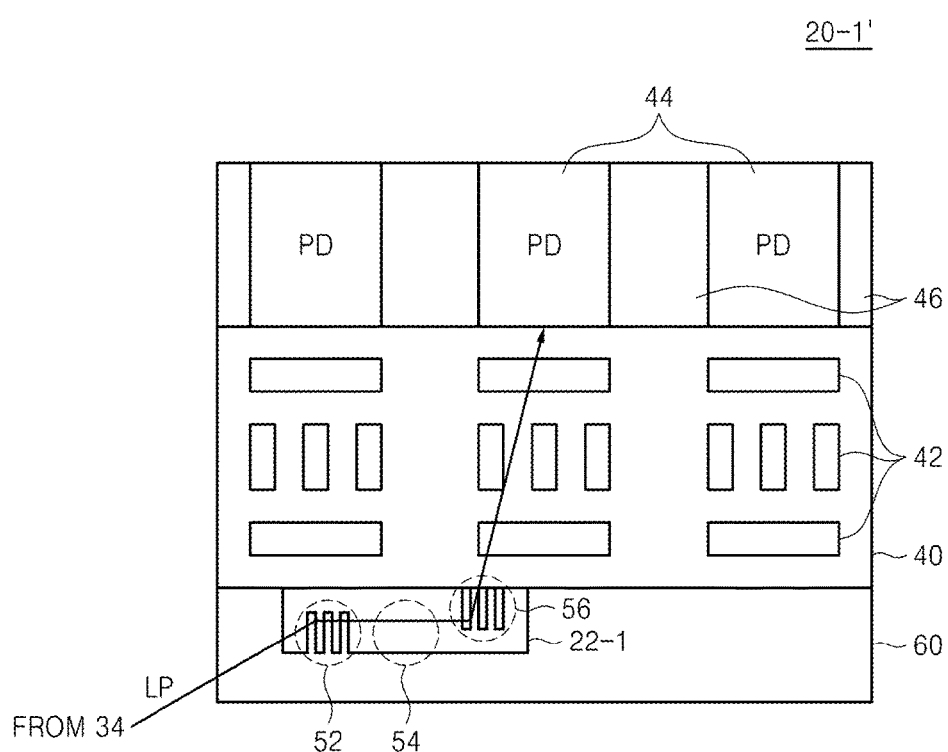
FIG. 11 is a cross-sectional view of a part of the sensor array shown in FIG. 2 according to other example embodiments of the inventive concepts.

FIG. 11 is a cross-sectional view of a part of the sensor array shown in FIG. 2 according to other example embodiments of the inventive concepts.

Referring to FIGS. 2 and 11, a part of the sensor array 20-1' according to the example embodiments of the sensor array 20-1 shown in FIG. 2 includes a biosensor 22-1 between a sustain wafer layer 60 and a metal line layer 42. A back side illumination image sensor (BIS) may include the biosensor 22-1 according to example embodiments of the inventive concepts.

The biosensor 22-1 is formed below the metal line layer 42 in the BIS manufacturing process and is covered with the sustain wafer layer 60. Noise of the biosensor 22-1 may be reduced due to the sustain wafer layer 60. A light pattern transmitted from a light source 34 undergoes coupling by a first grating coupler 52, passes through a bio-sensing region 54, and is output to photoelectric conversion devices 44 embodied at the rear side by a second grating coupler 56.

Figure 12:
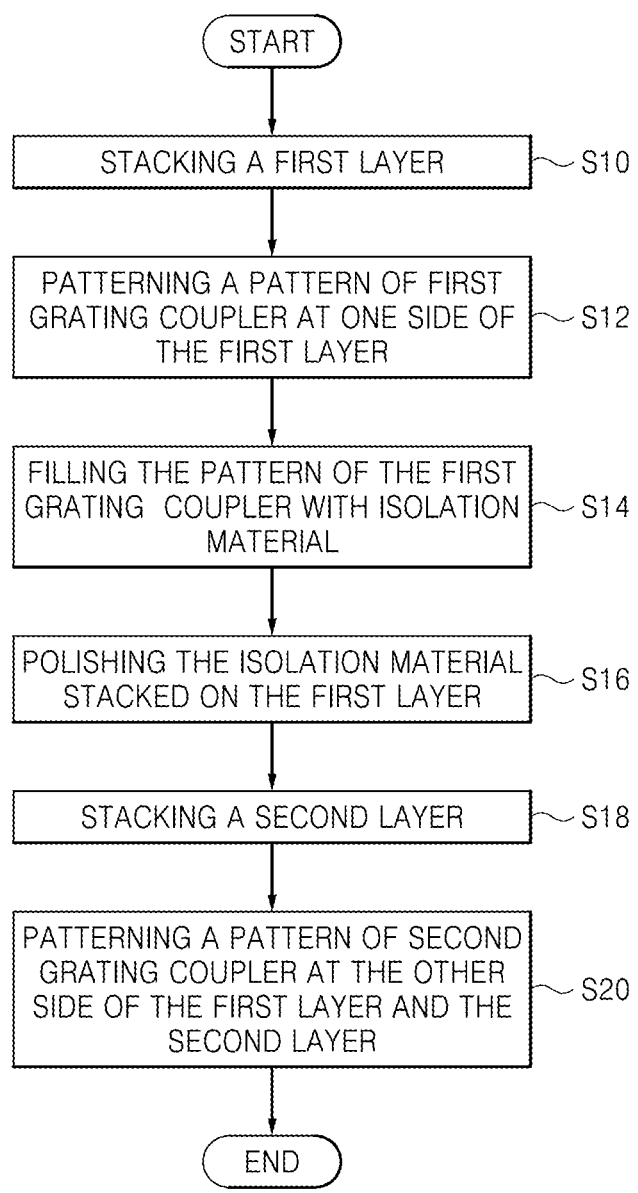
FIG. 12 is a flow chart of a method for manufacturing the biosensor according to example embodiments of the inventive concepts.

FIG. 12 is a flow chart of a method for manufacturing the biosensor according to example embodiments of the inventive concepts.

Referring to FIGS. 4 through 9, and 12, the first layer 62 is stacked on the insulating layer 48 (S10), and then, the pattern of the second grating coupler 56 may be patterned at one side of the stacked first layer 62, for example, on the right of the stacked layer 62 (S12).

The pattern of the second grating coupler 56 is filled with isolation material 64 (S14), the isolation material 64 stacked on the first layer 62 is polished (S16). The second layer 66 is stacked on the first layer 62 (S18), and the pattern of first grating coupler 52 is patterned on the first layer 62 and the stacked second layer 66 (S20).

Figure 13:
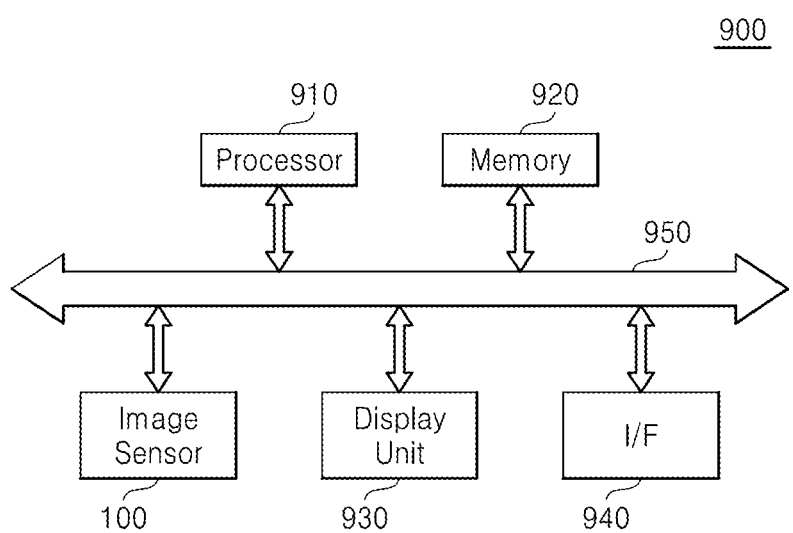
FIG. 13 is a block diagram of a system including the bio-image sensor of FIG. 1 according to example embodiments of the inventive concepts.

FIG. 13 is a block diagram of a system including the bio-image sensor of FIG. 1.

Referring to FIGS. 1 and 13, an image processing system 900 includes the bio-image sensor 100 of FIG. 1, a processor 910, a memory 920, a display unit 930, and an interface 940.

The image processing system 900 may be embodied into a medical device or mobile device. The mobile device may be embodied into a mobile phone, smart phone, tablet PC, personal digital assistant (PDA), enterprise digital assistant (EDA), portable multimedia player (PMP), e-book, or the like.

The processor 910 controls the operation of the bio-image sensor 100 and processes image data output from the bio-image sensor 100. For example, the processor 910 may generate two-dimensional or three-dimensional image data based on color information, depth information, and/or motion information output from the bio-image sensor 100. The processor 910 may denote the ISP 200.

The memory 920 may store a program for controlling the operation of the bio-image sensor 100 through a bus 950 and an image generated in the processor 910, and the processor 910 may access the stored information and execute the program. The memory 920 may be embodied into a non-volatile memory.

The display unit 930 receives the image from the processor 910 or the memory 920 and displays the same through a display, for example, Liquid Crystal Display (LCD), LED display, OLED display, Active Matrix Organic Light Emitting Diodes (AMOLED) display, or flexible display.

The interface 940 may be embodied into the interface for inputting/outputting an two-dimensional or three-dimensional image. The interface 940 may be embodied into a wireless interface.

Figure 14:
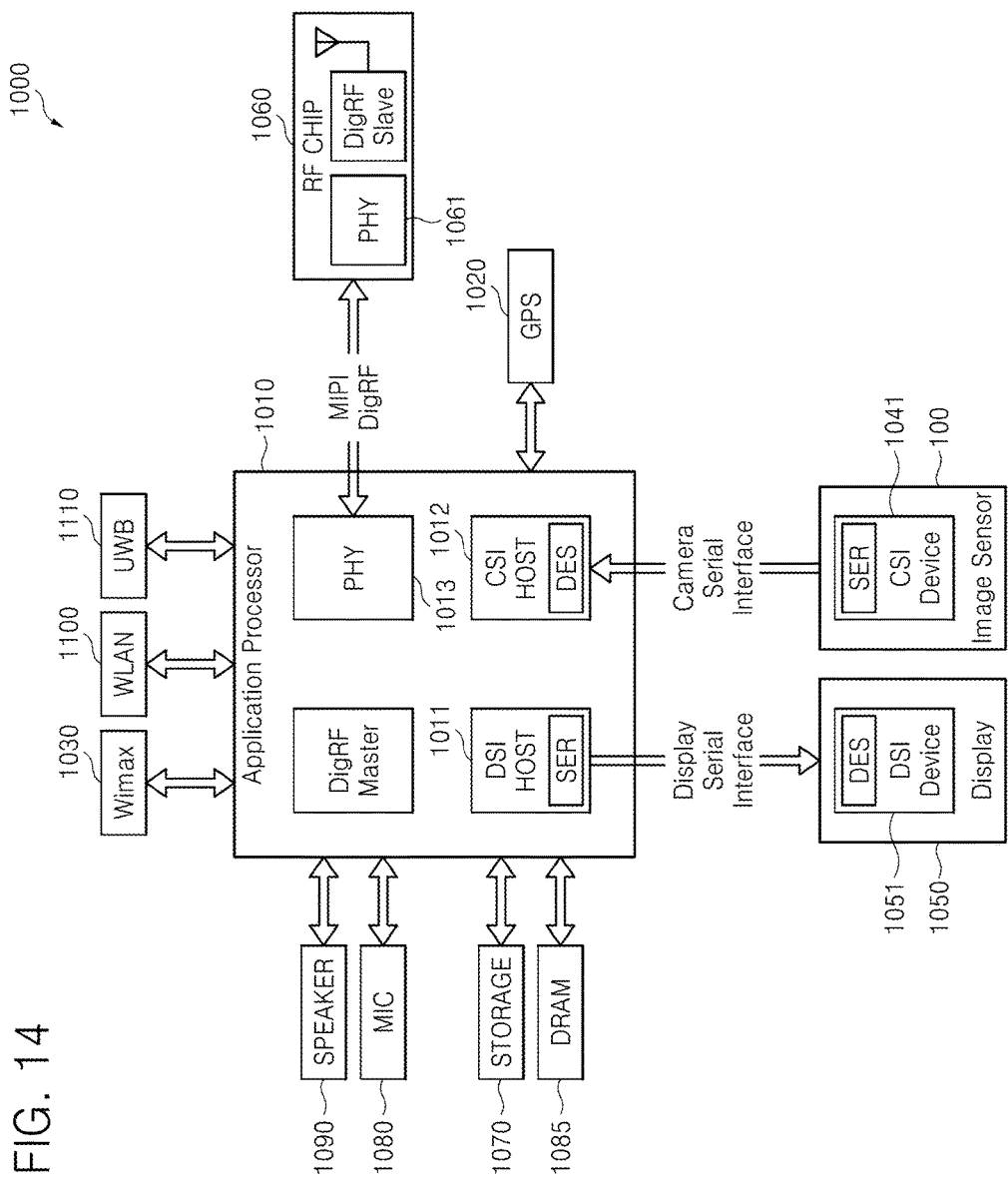
FIG. 14 is a block diagram of a system including the bio-image sensor of FIG. 1 according to other example embodiments of the inventive concepts.

FIG. 14 is a block diagram of a system including the bio-image sensor of FIG. 1 according to other example embodiments.

Referring to FIGS. 1 and 14, an electronic system 1000 may be embodied into a data processing device that can use or apply a mobile industry processor interface (MIPI), for example, personal digital assistants (PDA), portable multimedia player (PMP), internet protocol television (IPTV) or smart phone.

The electronic system 1000 includes the bio-image sensor 100 of FIG. 1, an application processor 1010, and a display 1050.

A camera serial interface (CSI) host 1012 embodied in the application processor 1010 may perform a serial communication with a CSI device 1041 of the image sensor 100 through a camera serial interface (CSI). At this time, for example, the CSI host 1012 may include a deserializer (DES), and the CSI device 1041 may include a serializer (SER).

A DSI host 1011 embodied in the application processor 1010 may perform a serial communication with a DSI device 1051 of the display 1050 through a display serial interface (DSI). At this time, for example, the DSI host 1011 may include a serializer (SER), and the DSI device 1051 may include a deserializer DES.

The electronic system 1000 may further include an RF chip 1060 that can communicate with the application processor 1010. A physical layer (PHY) 1013 included in the application processor 1010 and a PHY 1061 included in the RF chip 1060 may exchange data according to MIPI DigRF.

The electronic system 1000 may further include a GPS 1020, a storage 1070, a microphone MIC 1080, a dynamic random access memory (DRAM) 1085, and a speaker 1090. The electronic system 1000 communicates through a wireless lan (WLAN) 1100 and/or an ultra wideband (UWB) 1110.

The method and the apparatus according to example embodiments of the inventive concepts have an effect of increasing a sensing speed of biomaterial by coupling the light pattern provided to the front of the optical biosensor by using the grating coupler of the input terminal and outputting the coupled light pattern to the CMOS image sensor (CIS) formed on the rear of the optical biosensor directly. Also, the method and the apparatus process the light pattern output from the optical biosensor by using the CSI, thereby simplifying the structure of the bio-sensing system and reducing a size of the bio-sensing system.

The foregoing is illustrative of example embodiments and is not to be construed as limiting thereof. Although a few example embodiments have been described, those skilled in the art will readily appreciate that many modifications are possible in example embodiments without materially departing from the novel teachings. Accordingly, all such modifications are intended to be included within the scope of the disclosure as defined in the claims. Therefore, it is to be understood that the foregoing is illustrative of various example embodiments and is not to be construed as limited to the specific embodiments disclosed, and that modifications to the disclosed embodiments, as well as other embodiments, are intended to be included within the scope of the appended claims.

What is claimed is:

1. An optical biosensor, comprising:
a first layer;
a second layer stacked on top of the first layer;
a first grating coupler within the first layer and the second layer, wherein the first grating coupler is configured to couple a light pattern that is provided to a top surface of the second layer; and
a second grating coupler within the first layer, the second grating coupler not extending into the second layer, wherein the second grating coupler is configured to output the coupled light pattern to a photoelectric conversion device via a bottom surface of the first layer.

2. The optical biosensor of claim 1, wherein a depth of the first grating coupler and a depth of the second grating coupler are same, and
a thickness of the first layer is identical to the depth of the second grating coupler.

3. The optical biosensor of claim 1, further comprising:
a light resonator configured to sense biomaterial by using the light pattern coupled by the first grating coupler.

4. The optical biosensor of claim 3, wherein the light resonator is a ring resonator.

5. The optical biosensor of claim 3, wherein the light pattern is output from the light resonator, further comprising:
an optical spectrometer configured to disperse the light pattern.

6. The optical biosensor of claim 5, wherein the optical spectrometer includes a plurality of ring resonators.

7. A bio-image sensor, comprising:
the optical biosensor according to claim 1;
the photoelectric conversion device coupled to the optical biosensor;
a metal line layer below the photoelectric conversion device; and
a sustain wafer layer below the metal line layer, wherein the optical biosensor is between the metal line layer and the sustain wafer layer.

* * * * *